(12) United States Patent
Ruff

(10) Patent No.: US 9,375,546 B2
(45) Date of Patent: Jun. 28, 2016

(54) PERSONAL AIRWAY HUMIDIFICATION AND OXYGEN-ENRICHMENT APPARATUS AND METHOD

(71) Applicant: William Henry Ruff, Valparaiso, IN (US)

(72) Inventor: William Henry Ruff, Valparaiso, IN (US)

( * ) Notice: Subject to any disclaimer, the term of this patent is extended or adjusted under 35 U.S.C. 154(b) by 316 days.

(21) Appl. No.: 13/927,185

(22) Filed: Jun. 26, 2013

(65) Prior Publication Data

US 2013/0340755 A1 Dec. 26, 2013

Related U.S. Application Data

(60) Provisional application No. 61/664,263, filed on Jun. 26, 2012.

(51) Int. Cl.
*A61M 16/16* (2006.01)
*A61M 16/10* (2006.01)
*B01D 53/22* (2006.01)

(52) U.S. Cl.
CPC ......... *A61M 16/1045* (2013.01); *A61M 16/101* (2014.02); *A61M 16/109* (2014.02); *A61M 16/1075* (2013.01); *A61M 16/16* (2013.01); *A61M 2202/0208* (2013.01); *B01D 2053/221* (2013.01); *B01D 2256/12* (2013.01); *B01D 2259/4533* (2013.01)

(58) Field of Classification Search
CPC ............... A61M 16/1045; A61M 16/1075; A61M 16/16; A61M 2202/0208; A61M 16/109; A61M 16/101; A61M 16/145; B01D 2259/4533; B01D 2053/221; B01D 2256/12; B01F 5/0476; B01F 261/104
USPC ....................................... 261/104
See application file for complete search history.

(56) References Cited

U.S. PATENT DOCUMENTS

| | | | | | |
|---|---|---|---|---|---|
| 3,304,011 | A | * | 2/1967 | Paasche | 239/305 |
| 3,434,471 | A | * | 3/1969 | Liston | 128/203.14 |
| 4,273,120 | A | | 6/1981 | Oswell | |
| 4,381,267 | A | | 4/1983 | Jackson | |
| 4,632,677 | A | * | 12/1986 | Blackmer | 96/7 |
| 4,769,146 | A | | 9/1988 | Schmidt | |
| 4,773,410 | A | | 9/1988 | Blackmer et al. | |
| 4,859,331 | A | | 8/1989 | Sachtler et al. | |

(Continued)

FOREIGN PATENT DOCUMENTS

GB 1352142 A * 5/1974

*Primary Examiner* — Jason Flick
*Assistant Examiner* — Victoria Leszczak
(74) *Attorney, Agent, or Firm* — Hartman Global IP Law; Gary M. Hartman; Domenica N. S. Hartman

(57) ABSTRACT

A personal airway humidification and oxygen-enrichment apparatus includes at least two membranes adapted to produce a conditioned gas. At least a first of the membranes is adapted to produce a first gas and at least a second of the membranes is adapted to produce a second gas having an oxygen content higher than the first gas. The conditioned gas includes the first gas, the second gas, or a combination thereof from the membranes. The membranes are adapted to produce the first gas and the second gas so that the conditioned gas contains gaseous water to about 100 percent saturation. The apparatus includes means for delivering water to the membranes, means for delivering an initial gas to the membranes, and a delivery hose adapted to receive the conditioned gas from one or more of the membranes and deliver the conditioned gas to a delivery device.

18 Claims, 3 Drawing Sheets

(56) References Cited

U.S. PATENT DOCUMENTS

| | | | |
|---|---|---|---|
| 5,078,130 A | 1/1992 | Van Oosten | |
| 5,109,471 A | 4/1992 | Lang | |
| 5,236,586 A | 8/1993 | Antoni et al. | |
| 5,411,018 A | 5/1995 | Rinehart | |
| 5,692,095 A | 11/1997 | Young | |
| 5,870,525 A | 2/1999 | Young | |
| 5,906,201 A | 5/1999 | Nilson | |
| 6,162,046 A | 12/2000 | Young et al. | |
| 6,347,936 B1 | 2/2002 | Young et al. | |
| 6,349,724 B1 | 2/2002 | Burton et al. | |
| 6,367,472 B1 | 4/2002 | Koch | |
| 6,585,509 B2 | 7/2003 | Young et al. | |
| 6,634,864 B1 | 10/2003 | Young et al. | |
| 7,014,765 B2 | 3/2006 | Dannenmaier | |
| 7,331,342 B2 | 2/2008 | Spearman et al. | |
| 7,431,570 B2 | 10/2008 | Young et al. | |
| 7,543,584 B2 | 6/2009 | Brookman | |
| 7,708,013 B2 | 5/2010 | Niland et al. | |
| 7,753,991 B2 | 7/2010 | Kertzman | |
| 8,146,590 B2 | 4/2012 | Nitta | |
| 2007/0083677 A1 | 4/2007 | Cecka et al. | |
| 2009/0220222 A1 | 9/2009 | Rabin et al. | |
| 2009/0224064 A1 | 9/2009 | Brodbeck et al. | |
| 2009/0324206 A1 | 12/2009 | Young et al. | |
| 2010/0142934 A1 | 6/2010 | Sellers et al. | |
| 2011/0210458 A1 | 9/2011 | Brodbeck et al. | |
| 2015/0165146 A1 | 6/2015 | Bowman et al. | |

\* cited by examiner

PERSONAL AIRWAY HUMIDIFICATION AND OXYGEN-ENRICHMENT APPARATUS AND METHOD

CROSS REFERENCE TO RELATED APPLICATIONS

This application claims the benefit of U.S. Provisional Application No. 61/664,263, filed Jun. 26, 2012, the contents of which are incorporated herein by reference.

BACKGROUND OF THE INVENTION

The present invention generally relates to devices for personal airway humidification. More particularly, this invention relates to a personal airway humidification apparatus adapted to provide humidified air, oxygen-enriched air, or combination thereof to a patient.

It is a well-known and acknowledged concept that breathing plays a role in systemic fluid balance, chemical balance, and temperature control in a patient's body. Personal humidification devices are commonly utilized to provide a water saturated air to a patient in order to treat a variety of conditions. The literature involving the medical use of gaseous water and findings relating to such uses is voluminous. In addition to the humidity level of the air, the oxygen content is also known to be important to the treatment of patients. As an example, oxygen-enriched air is commonly used on patients for respiratory treatment. Ideally, the water saturated air has 100 percent water saturation, as lower saturation amounts may cause dehydration rather than hydration, and is at an elevated temperature adequate to promote mucus mobility (i.e., reduce mucus retention).

A variety of devices have been developed and manufactured for use as personal humidification devices, with the object of promoting pulmonary hygiene and bronchial dilation in a patient. Personal humidification devices deliver humidified air directly to the respiratory airway of patients, and as such do not include room humidifiers. Related devices include devices disclosed in U.S. Pat. No. 4,773,410, devices manufactured by the OECO Corporation and Gulfstream, various aerosol-producing or nebulization devices, CPAP and BIPAP devices manufactured by Respironics, Res-med, Fisher Paykel and others, and Vapotherm high-flow technology devices. Various steam humidifiers and facial saunas are also known personal devices that are intended for short-term use.

Personal humidification devices of the types disclosed by U.S. Pat. No. 4,773,410 and manufactured by the OECO Corporation and Gulfstream are fairly large heavy machines and employ pumps to force humidified air through small bore tubing and simple nasal cannulas. These devices are uniquely capable of providing humidification effectively and efficiently to a sleeping subject. However, they often produce noise levels that may disturb the user and others nearby. In addition, the devices can be expensive to own and operate, and may require professional cleaning and maintenance.

Aerosol devices are small, portable and usually inexpensive. However, these devices employ sub-droplet liquid phase water (rather than the preferred gaseous or molecular phase water) which can transport viruses and bacteria to the user. In addition, the inhalation of nebulized water can cause broncho-spasm. These devices can be used to transport medication, but their uses for other treatment purposes have been questioned. Medically-supervised use may be advisable due to increased risk of broncho-spasm and potential for bacterial and/or viral inoculation, and therefore aerosol devices are not generally prescribed for personal humidification performed at the patient's home.

CPAP, BIPAP, high-flow, and blow-over technology devices tend to be light, quiet, portable and provide varying levels of humidification. However, these devices rarely provide 100 percent water-saturated air. In addition, few of these devices employ heated delivery and fewer employ monitored heated delivery. Generally, these devises use high-flow, fan-driven technologies that use large bore tubing and very uncomfortable and clumsy face masks or cannulas. While designed for sleep use, these devices tend to be the least comfortable and cannot compete for comfort with small-bore, heat-monitored pump-driven equipment. Consequently, many patients spend thousands of dollars on home equipment of this type only to discover that they dislike them causing compliance to prescribed use to be inconsistent at best.

Personal heated humidifiers such as steam humidifiers and facial saunas are well suited for humidifying an individual's airway. These devices are typically small, portable and relatively inexpensive. Unfortunately, these devices are generally limited to short-term use only. For example, these devices are typically designed for fifteen to thirty minutes of continuous use, and may require the user to bend over the device throughout this period of time. As with room humidifying steamers, other activities are nearly impossible while using personal humidifiers.

In addition to the above limitations, the previously described devices rarely provide oxygen-enriched air. Producing oxygen-enriched air that is simultaneously humidified has thus far been deemed uneconomical or impractical. However, there are medical conditions which would benefit from treatment with a humidified and oxygen-enriched air. Consequently, there is a demand for a device capable of providing such air, in addition to providing personal, convenient, and long-term use.

In view of the above, it can be appreciated that there are certain problems, shortcomings and disadvantages associated with the prior art, and that it would be desirable to develop an apparatus capable of providing an oxygen-enriched air having 100 percent gaseous water saturation to a patient.

BRIEF DESCRIPTION OF THE INVENTION

The present invention provides an apparatus and method suitable for personal airway humidification and capable of oxygen-enrichment to provide to a patient an oxygen-enriched air characterized by having 100 percent gaseous water saturation.

According to a first aspect of the invention, a personal airway humidification and oxygen-enrichment apparatus includes at least two membranes adapted to produce a conditioned gas. At least a first of the membranes is adapted to produce a first gas and at least a second of the membranes is adapted to produce a second gas having an oxygen content higher than the first gas. The conditioned gas includes the first gas, the second gas, or a combination thereof from the membranes. The membranes are adapted to produce the first gas and the second gas so that the conditioned gas contains gaseous water to about 100 percent saturation. The apparatus includes means for delivering water to the membranes, means for delivering an initial gas to the membranes, and a delivery hose adapted to receive the conditioned gas from one or more of the membranes and deliver the conditioned gas to a delivery device.

According to a second aspect of the invention, a method of personal airway humidification and oxygen-enrichment includes providing at least two membranes adapted to produce a conditioned gas. At least a first of the membranes is adapted to produce a first gas and at least a second of the membranes is adapted to produce a second gas having an oxygen content higher than the first gas. The conditioned gas includes the first gas, the second gas, or a combination thereof from the membranes. The membranes are adapted to produce the first gas and the second gas so that the conditioned gas contains gaseous water to about 100 percent saturation. The method includes delivering water to the membranes, delivering an initial gas to the membranes, and delivering a conditioned gas from the membranes to a delivery device.

A technical effect of the present invention is the ability to produce and deliver a conditioned gas made up of at least one of at least two different deliverable gases, air and oxygen-enriched air, and further to produce the conditioned gas to have about 100 percent saturation with gaseous water. In particular, by selectively delivering water and air to two separate membranes, it is possible to selectively deliver to a patient either the air, the oxygen-enriched air, or any combination thereof.

Other aspects and advantages of this invention will be better appreciated from the following detailed description.

DETAILED DESCRIPTION OF THE INVENTION

The present invention is generally applicable to devices capable of delivering a conditioned breathable gas to a patient. Specifically, the invention combines a gaseous humidifier and an oxygen-enriching apparatus, such that the conditioned gas has a typical or increased oxygen content, relative to atmospheric air, and contains gaseous water to about 100 percent saturation and may be provided to a delivery device capable of delivering the conditioned gas to the patient. Unlike conventional personal humidification devices, for example, CPAP and BIPAP devices, the present invention preferably produces the conditioned gas with 100 percent gaseous water saturation (at the delivered temperature). Gas below 100 percent water saturation may cause dehydration rather than hydration in the patient. According to the present invention, this capability reduces potential shortcomings associated with conventional devices, for example, aerosol devices that may cause broncho-spasms and/or transmit viruses and bacteria.

Figure 1:
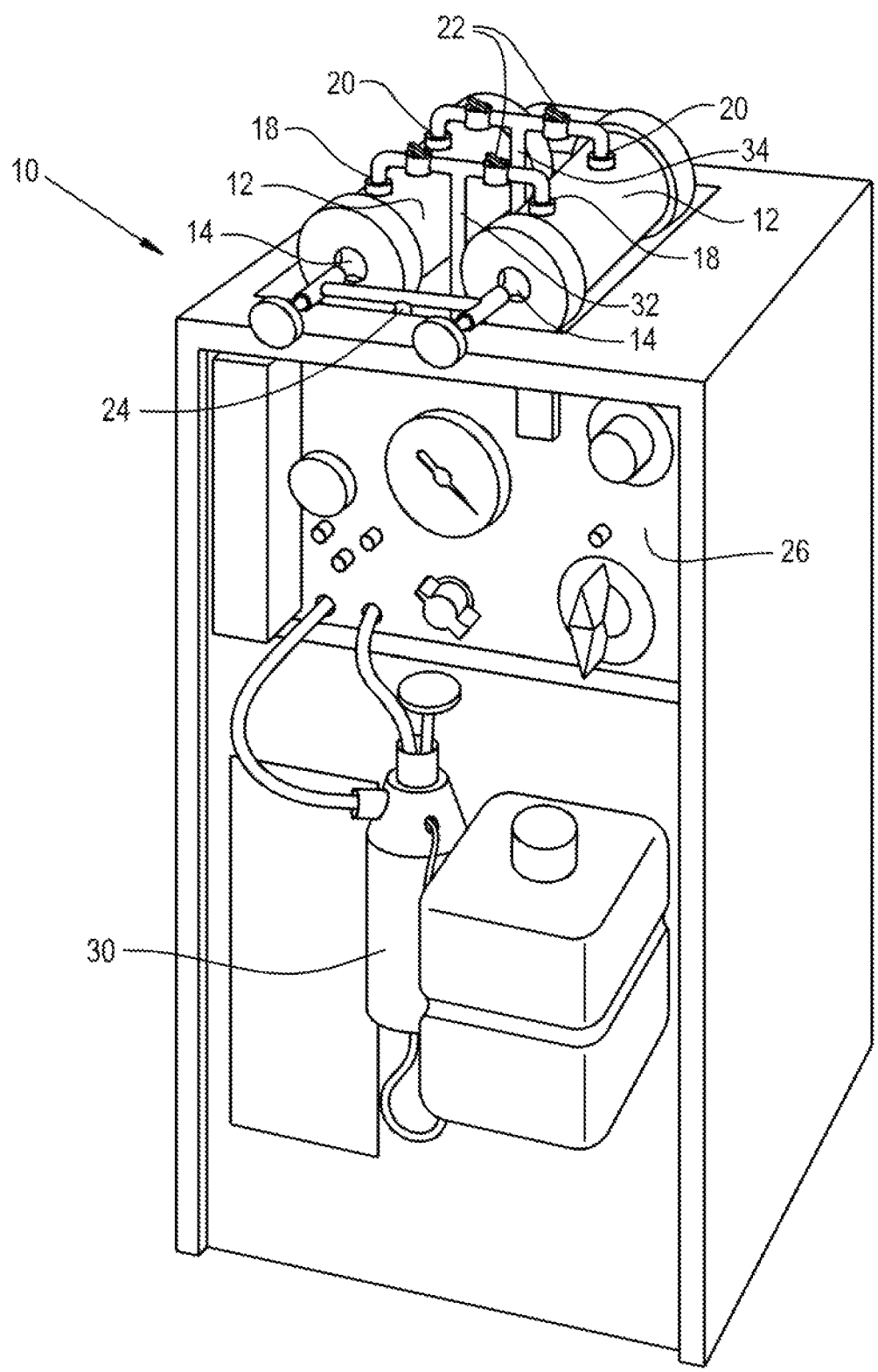
FIG. 1 is a perspective view representing a personal airway humidification apparatus in accordance with an aspect of the present invention.
Figure 2:
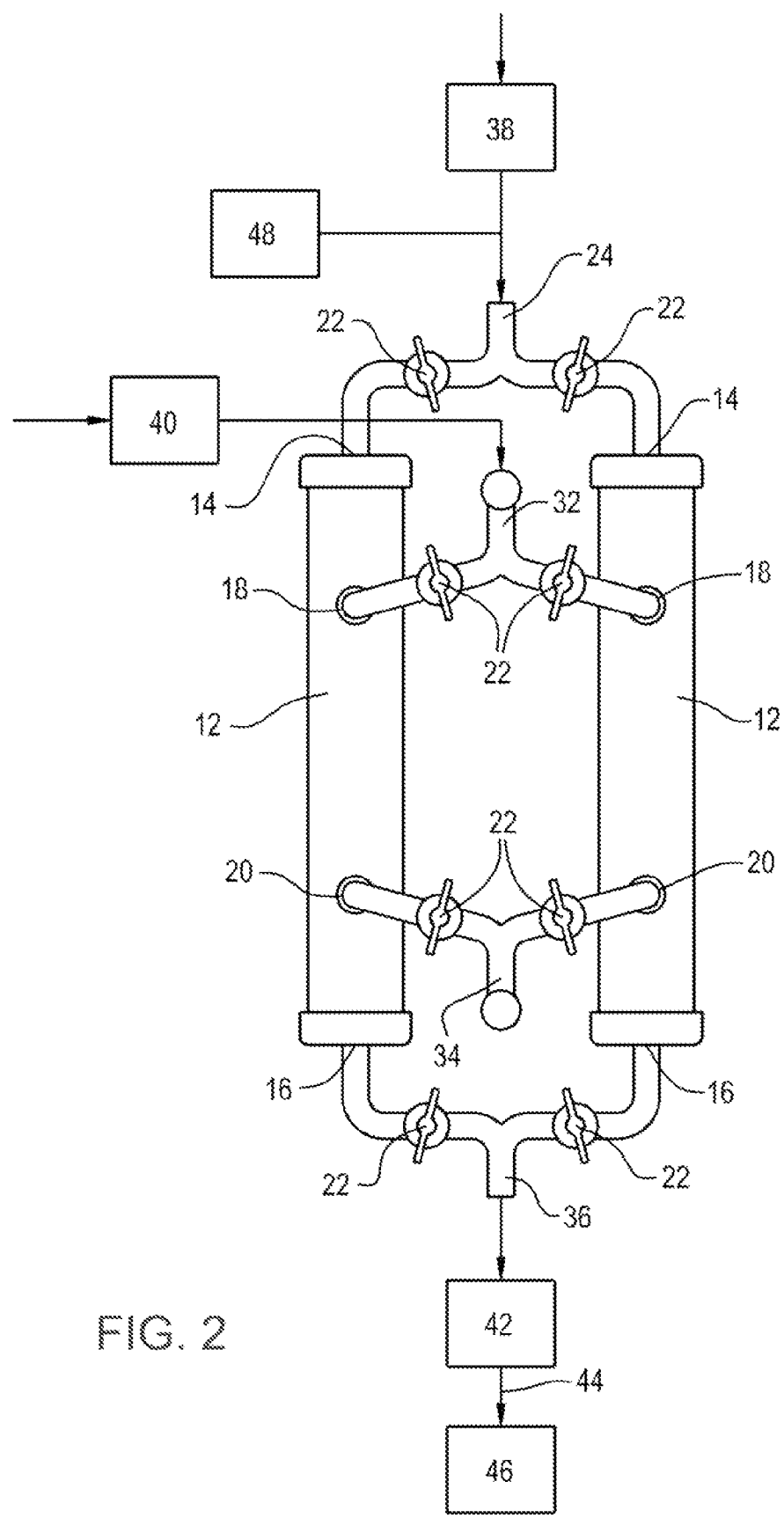
FIG. 2 is an isolated top view representing a pair of containers shown in FIG. 1 and comprising permeable membranes.

FIG. 1 represents a personal airway humidification and oxygen-enrichment apparatus 10 according to an embodiment of the present invention. The apparatus 10 comprises at least two permeable membranes (not shown) within containers 12, represented in an isolated view in FIG. 2. The membranes are adapted to produce two different breathable gases which may be delivered to the patient. The containers 12 housing the membranes are represented as being located on top of the apparatus 10, as shown in FIG. 1. However, this arrangement is for illustrative purposes only as other locations and containment configurations are foreseeable. For example, the containers 12 may be consolidated within a single containment structure and/or located within the interior of the apparatus 10. Additionally, while the containers 12 in FIGS. 1 and 2 are arranged parallel to each other, other configurations may be desirable for particular applications. The design and configuration of the containers 12 may or may not be distinguishable from one another.

The apparatus 10 can be configured to produce the conditioned gas from an initial gas comprising air drawn from the surrounding environment or from a reservoir 30. The initial gas is preferably filtered and sanitized prior to entering the containers 12. Suitable methods of filtering, sanitizing, transporting, and containing the initial gas are known to those skilled in personal humidification and respiration engineering, and will not be elaborated on herein. For purposes of brevity, nonlimiting examples of suitable methods can be found in U.S. Pat. No. 4,773,410. As represented in FIG. 2, the initial gas is fed into the containers 12 through air inlets 14 via tubing 24. The initial gas travels through the membranes within the containers 12 wherein the membranes interact with the initial gas to produce the conditioned gas. The conditioned gas then exits the containers 12 through air outlets 16 and is transported through tubing 36 to a delivery hose 44 and/or device 46 and ultimately to the patient's respiratory tract. The delivery device 46 may be a conventional cannula, a tracheal delivery device, or another delivery device known in the art, although small bore delivery hoses and devices are believed to be preferred. Preferably, the delivery device 46 does not cover portions of the patient's face other than the mouth and nose areas as allowing heated air to contact other areas of the patient's face may be uncomfortable for the patient.

Figure 3:
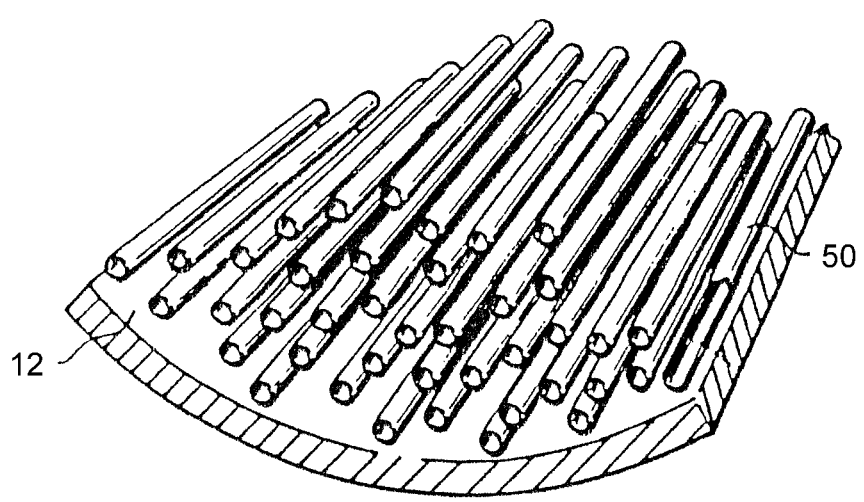
FIG. 3 is an internal sectional partial view of a nonlimiting example of the membranes of FIGS. 1 and 2.

The membranes are preferably formed of a fibrous material, and most preferably a polymer fiber material, though the use of other materials is also within the scope of the invention; for example, the membranes may be comprised of hollow fiber cartridges. FIG. 3 is an internal sectional partial view of a nonlimiting example of the membranes having hollow fiber material 50 within the container 12. Preferably, at least one of the membranes is adapted to produce atmospheric air (defined herein as air containing an amount of oxygen typical for standard atmospheric air, i.e. approximately 21 percent oxygen by volume when at a temperature of 15° C. and at a pressure of one atm), derived from the initial gas. The membrane within the other container 12 is preferably adapted to produce an oxygen-enriched air (defined herein as air containing greater than 21 percent oxygen by volume and up to about 40 percent oxygen by volume). The composition of the resulting conditioned gas produced by combining the air individually produced by the two membranes, as well as the compositions of the individual gases, will depend on the characteristics of each of the membranes. For example, the specific fibrous material used in an individual membrane will determine the chemical composition of the air produced by that individual membrane. In addition, the membranes may be adapted to act as viral and bacterial filters further reducing the risk of disease transmission.

In addition to conditioning the final composition of the conditioned gas, the membranes are each capable of humidifying the initial gas that it receives so that the conditioned gas contains gaseous water, preferably to about 100 percent saturation, and more preferably 100 percent saturation. As represented in FIG. 2, water is fed into the containers 12 through a water inlet 18 via tubing 32. Within the containers 12, the water travels through a series of liquid-vapor and gas-vapor boundaries created by the membranes. This process saturates the initial gas flowing through the membranes with gaseous water. Once the initial gas is saturated to a predetermined amount, excess water is filtered out of the containers 12 through water outlets 20 by means of tubing 34, as shown in FIG. 2. Depending on the specific membranes utilized, the resulting conditioned gas preferably comprises atmospheric air, oxygen-enriched air, or combination thereof having 100 percent water saturation. Importantly, the conditioned gas contains molecular water, and does not contain droplets or micro-droplets of water. This reduces the likelihood that the patient will suffer from broncho-spasms or will be infected with viruses or bacteria as a result of breathing the conditioned gas. In addition, because the conditioned gas is saturated with water, its flammability will be comparable to standard air regardless of the oxygen content.

As represented in FIGS. 1 and 2, the apparatus 10 includes a plurality of valves 22, for example, stop-cock valves, for switching between the membranes. Specifically, opening all of the valves 22 on the tubing 24, 32, 34, and 36 corresponding to an individual container 12 allows the initial gas and water to enter the individual container 12. Conversely, closing all of the valves 22 on the tubing 24, 32, 34, and 36 corresponding to an individual container 12 restricts the initial gas and water from entering the container 12. Manipulation of the valves 22 provides the capability to selectively utilize the membranes and thereby control the composition of the resulting conditioned gas, for example, to contain various levels of oxygen as a result of varying the relative amounts of the atmospheric and oxygen-enriched air present in the conditioned gas. The valves 22 may be of any suitable type known in the art, and may be mechanically or electrically controlled either manually or through an automated control system (not shown) whose controls may be located on a control panel 26 on the face of the apparatus 10. While the invention has been described herein as utilizing the valves 22 to switch between the containers 12, any means known in the art for switching between the containers 12 is within the scope of the invention.

According to a preferred aspect of the invention, the tubing 24, 32, 34, and 36 attached to the air inlet 14, the air outlet 16, the water inlet 18, or the water outlet 20, respectively, connects with the corresponding inlet 14/18 or outlet 16/20 of all other containers 12 on the apparatus 10. For example, FIG. 2 represents the tubing 24 attached to the air inlet 14 on both of the containers 12 as joining at a "Y" connection with a single inlet. Similar configurations are represented for the air outlet 16, the water inlet 18, and the water outlet 20 and their corresponding tubing 32, 34, and 36, respectively. Connecting the corresponding inlets 14 and 18 and outlets 16 and 20 of each individual container 12 to a single inlet and/or outlet provides the capability to provide the initial gas and water to all containers 12 with a single air source and a single water source, respectively. Importantly, connecting the air outlets 16 to a single outlet provides the capability of providing the conditioned gas from any one or more membranes to a single delivery hose 44 or device 46, regardless of the number of membranes used. As a result, the conditioned gas may be modified without the need for the patient to change delivery devices.

The apparatus 10 may be adapted to regulate the temperature of the water supplied to the membranes to a predetermined operating temperature, for example with a water heating control device 40. Alternatively or in addition to the above, the apparatus 10 may be adapted to regulate the temperature of the initial gas prior to entering the containers 12, for example with a heating control device 38. In a preferred embodiment, the conditioned gas is regulated in the delivery hose 44; for example, with a heating control device 42 and/or insulation. Regulation of the temperature of the water, initial gas, and/or conditioned gas may be separately controlled, and the respective temperatures can be displayed, for example, on the control panel 26 on the face of the apparatus 10 as represented in FIG. 1. The temperature of the water, initial gas, and/or conditioned gas is preferably maintained so that the conditioned gas provided to the patient is at temperatures of between about 75° F. (about 24° C.) and any maximum temperature that the patient can comfortably breath, for example, about 110° F. (about 43° C.). Ideally, the conditioned gas is at an elevated temperature adequate to promote mucus mobility (i.e., reduce mucus retention). Investigations leading to the present invention determined that the temperature is preferably at least 85° F. (about 29° C.) in order to promote mucus mobility, and more preferably the temperature is above the core body temperature of the patient, generally 98.6° F. (about 37° C.) or higher.

The apparatus 10 additionally may be adapted for providing pressure to the flow of the initial gas through the membranes, and may be further adapted for regulating the pressure or flow rate of the conditioned gas to a predetermined operating level. The flow rate of the conditioned gas from the apparatus 10 to the patient is preferably at or near a maximum flow rate that the patient can comfortably breathe based on their lung capacity, physiology, and condition. For example, the flow rate may be between about five (for a child) and about fifty (for a healthy adult) liters per minute, though higher and lower flow rates are foreseeable. The flow rate of the conditioned gas may be regulated and adjusted using controls and/or a display on the apparatus 10, such as those represented in FIG. 1 on the control panel 26. The flow rate capabilities may be different between the individual membranes depending on their individual configuration and construction materials. The process of delivering the water, and the initial gas, and conditioned gas through the apparatus 10 as well as the process of pressurizing the flow of the water and the initial gas through the membranes are well within the capabilities of those skilled in respiration science and engineering, and will not be elaborated on in the present application. It should be sufficient to note that a pressure pump 48 can be used for pressurizing the flow through the membranes.

According to preferred aspects of the invention, the apparatus 10 may be nearly noise and heat neutral and is adapted for safe continuous use, for example, up to ten hours or more. For example, the apparatus 10 may need to be cooled to reduce any produced radiated or conducted heat. With such capabilities, patients may be more likely to continuously use the apparatus 10 as prescribed and may therefore be more likely to recover from their ailments.

While the invention has been described in terms of specific embodiments, it is apparent that other forms could be adopted by one skilled in the art. For example, the physical configuration of the apparatus 10 could differ from that shown, and materials and processes other than those noted could be used. Therefore, the scope of the invention is to be limited only by the following claims.

The invention claimed is:

1. A personal airway humidification and oxygen-enrichment apparatus that produces and delivers a breathable conditioned gas at a delivered temperature of at least 24° C. to the respiratory tract of a patient through a delivery device, the apparatus comprising:

at least two containers each containing a membrane, the membrane of a first of the at least two containers comprising a first hollow fiber material adapted to produce a breathable first gas containing gaseous water at 100 percent saturation at the delivered temperature but does not contain droplets or micro-droplets of water, and the membrane of a second of the at least two containers comprising a second hollow fiber material that is different from the first hollow fiber material and adapted to produce a breathable second gas containing oxygen-enriched air having an oxygen content by volume higher than the first gas and gaseous water at 100 percent saturation at the delivered temperature but does not contain droplets or micro-droplets of water;

a tubing connected to outlets of the at least two containers to selectively receive the first and second gases therefrom and yield at an outlet of the tubing, the conditioned gas comprising the first gas, the second gas, or a combination thereof from the at least two containers, the membranes of the at least two containers being adapted to produce the first gas and the second gas so that the conditioned gas at the outlet of the tubing contains gaseous water at about 100 percent saturation at the delivered temperature but not droplets or micro-droplets of water;

means for delivering an initial air to each of the at least two containers;

means for delivering water to each of the at least two containers, wherein the water travels through a series of liquid-vapor and gas-vapor boundaries within the membranes to increase a humidity level of the initial air and produce the first and second gases with the gaseous water thereof at 100 percent saturation at the delivered temperature; and a delivery hose coupled to the outlet of the tubing to receive the conditioned gas and deliver the conditioned gas directly to the respiratory tract of the patient through the delivery device at the delivered temperature and with the gaseous water at 100 percent saturation.

2. The personal airway humidification and oxygen-enrichment apparatus, according to claim 1, wherein the membrane of the first of the at least two containers is adapted to produce atmospheric air with the gaseous water at 100 percent saturation and the membrane of the second of the at least two containers is adapted to produce oxygen-enriched air with the gaseous water at 100 percent saturation and having up to about forty percent oxygen by volume.

3. The personal airway humidification and oxygen-enrichment apparatus according to claim 1, further comprising means for selectively switching between the at least two containers to provide the capability of producing the conditioned gas with one or more of the membranes of the at least two containers.

4. The personal airway humidification and oxygen-enrichment apparatus according to claim 1, further comprising means for regulating the delivered temperature of the conditioned gas.

5. The personal airway humidification and oxygen-enrichment apparatus according to claim 1, further comprising means for regulating the temperature of the initial air supplied to at least one of the at least two containers.

6. The personal airway humidification and oxygen-enrichment apparatus according to claim 1, further comprising means for regulating the temperature of the water supplied to at least one of the at least two containers.

7. The personal airway humidification and oxygen-enrichment apparatus according to claim 1, further comprising means for providing pressure to the flow of the initial air through at least one of the at least two containers.

8. The personal airway humidification and oxygen-enrichment apparatus according to claim 1, further comprising means for regulating the flow rate of the initial air through at least one of the at least two containers.

9. The personal airway humidification and oxygen-enrichment apparatus according to claim 1, further comprising means for regulating the flow rate of the conditioned gas through the delivery hose to the delivery device.

10. A method of personal airway humidification and oxygen-enrichment by producing and delivering a breathable conditioned gas at a delivered temperature of at least 24° C. to the respiratory tract of a patient through a delivery device, the method comprising:

providing a system comprising at least two containers each containing a membrane, the membrane of at least a first of the at least two containers comprising a first hollow fiber material adapted to produce a breathable first gas containing gaseous water at 100 percent saturation at the delivered temperature but does not contain droplets or micro-droplets of water, the membrane of at least a second of the at least two containers comprising a second hollow fiber material that is different from the first hollow fiber material and adapted to produce a second gas containing oxygen-enriched air having an oxygen content by volume higher than the first gas and gaseous water at 100 percent saturation at the delivered temperature, the at least two containers having outlets coupled to a tubing that selectively receives the first and second gases therefrom and yields at an outlet of the tubing, the conditioned gas comprising the first gas, the second gas, or a combination thereof from the at least two containers, the membranes of the at least two containers being adapted to produce the first gas and the second gas so that the conditioned gas at the outlet of the tubing contains gaseous water at 100 percent saturation at the delivered temperature but no droplet or micro-droplets of water;

delivering an initial air to each of the at least two containers;

delivering water to each of the at least two containers, wherein the water travels through a series of liquid-vapor and gas-vapor boundaries within the membranes to increase a humidity level of the initial air and produce the first and second gases with the gaseous water thereof at 100 percent saturation at the delivered temperature; and receiving the conditioned gas from the outlet of the tubing and delivering the conditioned gas directly to the respiratory tract of the patient through the delivery device at the delivered temperature and with the gaseous water at 100 percent saturation.

11. The method according to claim 10, wherein the membrane of the first of the at least two containers is adapted to produce atmospheric air with the gaseous water at 100 percent saturation and the membrane of the second of the at least two containers is adapted to produce oxygen-enriched air with the gaseous water at 100 percent saturation and having up to about forty percent oxygen by volume.

12. The method according to claim 10, further comprising controlling a level of oxygen in the conditioned gas by varying relative amounts of the first and second gas provided from one or more of the at least two containers.

13. The method according to claim 10, further comprising regulating the delivered temperature of the conditioned gas with a heating control device of the system.

14. The method according to claim 10, wherein the conditioned gas is 100 percent saturated with gaseous water and has a percent oxygen by volume of greater than atmospheric air.

15. The method according to claim 10, further comprising regulating the temperature of the water supplied to at least one of the at least two containers with a water heating control device.

16. The method according to claim 10, further comprising providing the conditioned gas to the patient with the delivery device, maintaining the delivered temperature of the conditioned gas with a heating control device of the system such that the conditioned gas is provided to the patient at a temperature of at least 29° C., wherein the conditioned gas is 100 percent saturated with gaseous water at the delivered temperature.

17. The method according to claim 10, further comprising regulating the flow rate of the initial air through at least one of the at least two containers with controls on the system.

18. The method according to claim 10, further comprising providing the conditioned gas from the delivery device to the patient and maintaining the delivered temperature of the conditioned gas with a heating control device of the system such that the conditioned gas is provided to the patient at a temperature above the core body temperature of the patient.

* * * * *